United States Patent [19]
Pigneul

[11] Patent Number: 5,478,336
[45] Date of Patent: Dec. 26, 1995

[54] SANITARY OR SIMILAR TOWEL WITH FLUID-IMPERMEABLE SIDE FLAPS

[75] Inventor: Raymond Pigneul, Durrenentzen, France

[73] Assignee: Kaysersberg, S.A., France

[21] Appl. No.: 774,363

[22] Filed: Oct. 8, 1991

Related U.S. Application Data

[63] Continuation of Ser. No. 358,381, filed as PCT/FR88/00469, Sep. 23, 1988, published as WO89/02729, Apr. 6, 1989, abandoned.

[30] Foreign Application Priority Data

Sep. 25, 1987 [FR] France ................... 87 132256

[51] Int. Cl.⁶ .......................... A61F 13/15; A61B 17/06
[52] U.S. Cl. .................. 604/385.1; 604/387; 604/389; 604/390; 206/438
[58] Field of Search ............. 604/385.1, 385.2, 604/386, 387, 389, 390, 391, 400, 401; 206/438, 440, 614

[56] References Cited

U.S. PATENT DOCUMENTS

| | | | |
|---|---|---|---|
| 3,421,502 | 1/1069 | Clair | 206/440 |
| 4,285,343 | 8/1981 | McNair | 604/387 |
| 4,402,689 | 9/1983 | Baum | 604/387 |
| 4,551,145 | 11/1985 | Ryan | 604/389 |
| 4,555,022 | 11/1985 | Eagon et al. | 206/438 |
| 4,608,047 | 8/1986 | Mattingly | 604/387 |
| 4,648,513 | 3/1987 | Newman | 206/614 |
| 4,710,178 | 10/1987 | Glaug et al. | 604/387 |
| 4,759,754 | 7/1988 | Korpman | 604/387 |
| 4,846,828 | 7/1989 | Mendelsonn | 604/387 |
| 4,857,066 | 8/1989 | Allison | 604/387 |
| 4,900,320 | 2/1990 | McCoy | 604/387 |
| 4,917,675 | 4/1990 | Taylor et al. | 206/440 |
| 5,637,417 | 8/1991 | Ternstrom et al. | 604/387 |

FOREIGN PATENT DOCUMENTS

| | | | |
|---|---|---|---|
| 0121966 | 10/1984 | European Pat. Off. | 604/387 |
| 0130848 | 1/1985 | European Pat. Off. | |
| 0134086 | 3/1985 | European Pat. Off. | |
| 0313426 | 4/1989 | European Pat. Off. | 601/387 |
| 2455885 | 12/1980 | France . | |
| 2494226 | 5/1982 | France | 604/387 |
| 1476726 | 6/1977 | United Kingdom | 604/387 |

*Primary Examiner*—Randall L. Green
*Assistant Examiner*—K. M. Reichle
*Attorney, Agent, or Firm*—Breiner & Breiner

[57] ABSTRACT

A sanitary towel having two side flaps designed to be folded around a folded sanitary towel after use to form a disposable package or small bag is described. The side flaps are preferably designed to form an integral part of a small protective pouch in which the sanitary towel is packaged prior to use. The invention obviates both the need for a separate package for disposal of the used sanitary towel and the use of independent individual packaging for the sanitary towels.

8 Claims, 2 Drawing Sheets

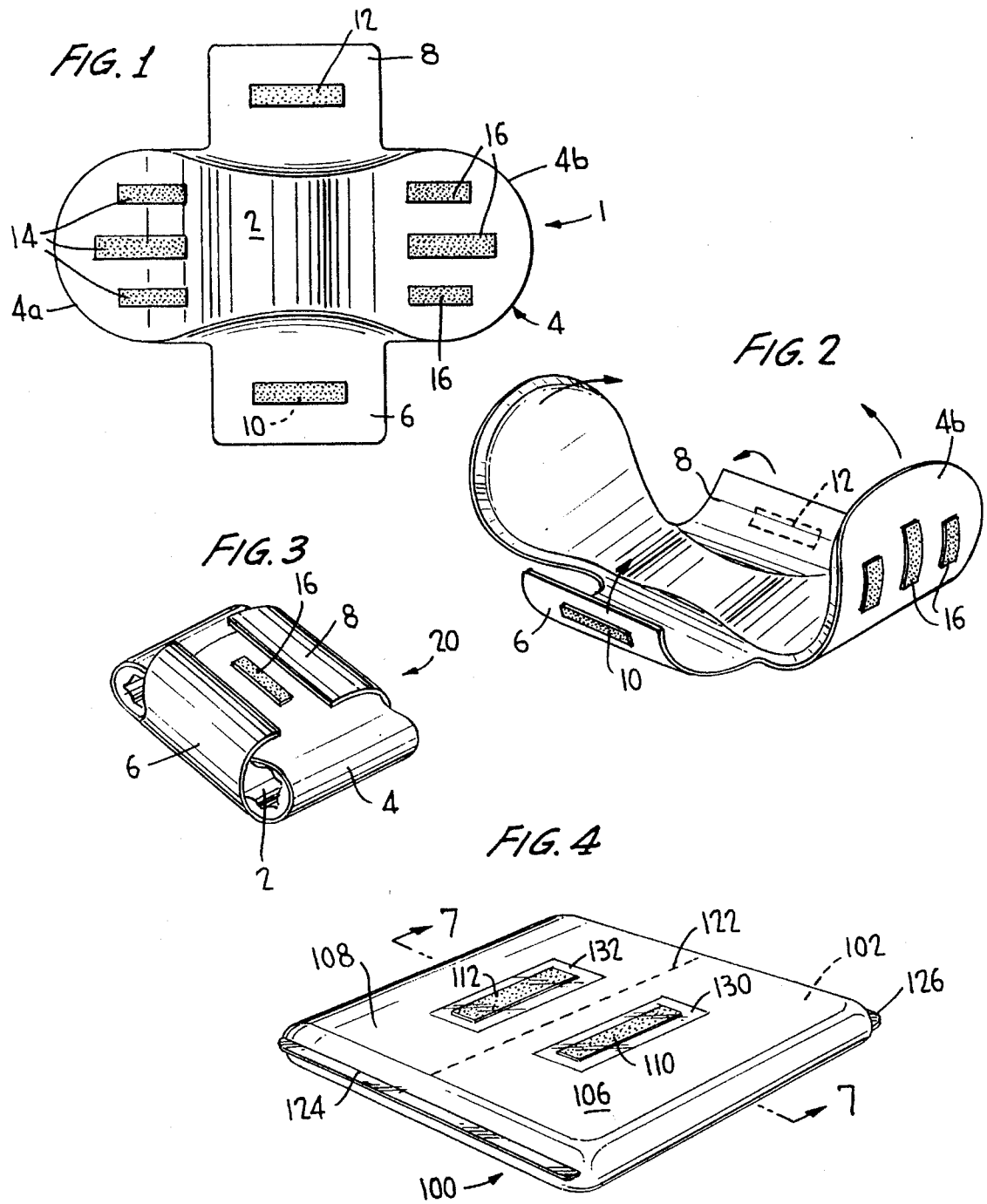

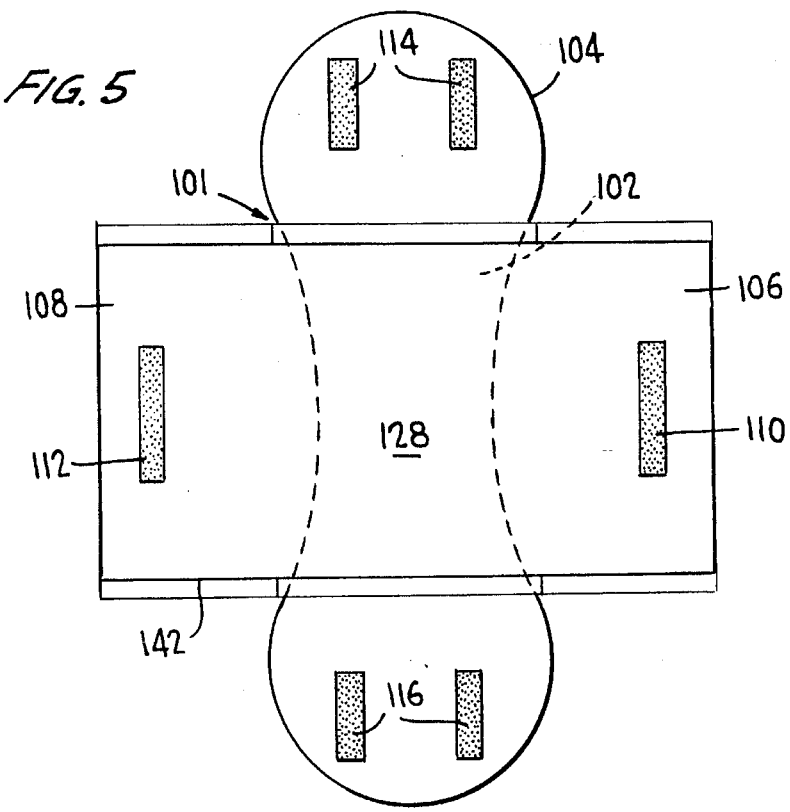

SANITARY OR SIMILAR TOWEL WITH FLUID-IMPERMEABLE SIDE FLAPS

This is a continuation of application Ser. No. 07/358,381, filed as PCT/FR88/00469, Sep. 23, 1988, published as WO89/02729, Apr. 6, 1989, now abandoned.

FIELD OF THE INVENTION

The subject of this invention is essentially a product consisting of a sanitary or similar towel with fluid-impermeable side flaps which are large enough to be tucked around the wearer's underwear. These side flaps are then folded to form a disposable packet for throwing the towel away after use, and preferably make up an integral part of a protective pouch.

BACKGROUND OF THE INVENTION

Document EP 0134086 has already described a sanitary or similar towel intended for feminine hygiene in particular and featuring a buffer element 216 for the absorption of fluids. It is fully contained in a sheath 214-230-234. The 214 part at least, which receives the fluids, is fluid permeable. Side flaps 224, 224' are intended to lessen the chance of leaks at the sides, in that these side flaps are arranged inside the wearer's underwear, with their ends folded against the inner edge 246 or 246' of the underwear.

It has been observed that these side flaps were not large enough to protect the underwear fully. These side flaps may also include moveable devices by which they are secured to the wearer's underwear, for example adhesive patches (see FIGS. 2, 4 and 7)

Document EP-A 0130848 describes a similar system, according to which the side flaps may also contain a fluid-absorbent pad inside.

Side flaps are also described in document FR-A 2455885. Another similar idea is described in U.S. Pat. No. 4,285,343, with the side flaps being tucked around the outside of the underwear, covering it completely by means of an overlapping arrangement (see FIGS. 2 and 5) or an edge-to-edge arrangement (FIG. 7), and once again including an absorbent material.

Document U.S. Pat. No. 4,608,047 also describes a sanitary towel with side flaps large enough to be tucked around the outside of the wearer's underpants, with at least one of these side flaps featuring a moveable device 34 for fixing the flap to the outside of the underwear and thus protecting it completely.

Moreover, document FR-A 2494226 describes a structure for the individual wrapping of hygiene products, including sanitary towels, before use, as well as a wrapping process using this structure.

In general, used sanitary towels are disposed of using a disposable packet supplied separately with the towels.

This constitutes an added complication for the user and increases production costs as well.

OBJECTS OF THE INVENTION

Thus, the purpose of this invention is to offer a technical solution that would eliminate the need for a separate wrapper in which to dispose of the used sanitary towel.

The invention is also intended to offer a technical solution that would eliminate the need for an individual wrapping that is separate from the towel itself.

BRIEF DESCRIPTION OF THE INVENTION

This invention offers the first simultaneous solution for both of these technical problems, using a very simple, inexpensive material suitable for use in mass production.

Thus, this invention offers a sanitary or similar napkin featuring a fluid-absorbent pad fully contained inside a sheath, with at least the portion receiving the fluids being fluid-permeable, and side flaps to reduce the risk of side leakage. These side flaps are large enough to be tucked around the outside of the wearer's underwear, and feature at least one moveable device for fixing them to the wearer's underwear in order to protect it fully. The side flaps are designed in such a way as to allow them to be folded around the used towel, once this towel itself has been folded, forming a disposable packet. The side flaps are also designed to form an integral part of a protective pouch in which the towel is packaged. The protective pouch is pre-stamped so that the side flaps are released when the protective pouch is opened. In accordance with a preferred design, the above-mentioned side flaps are formed by a single strip of fluid-impermeable material, e.g. a polythene film, advantageously joined to the actual towel.

The solution proposed by the invention thus offers a totally hermetic packaging for the towel, protecting it from contamination by dust and dirt before use. Because it is part of the towel, this packaging is also very economical.

According to one variation, the above-mentioned sheath containing the fluid-absorbent pad includes, on the outside of its front and back ends, moveable devices for fixing these ends to the wearer's underwear; these devices are also used to maintain the towel in the folded position. The devices for securing the flaps are advantageously placed near their outer edges, thus resulting in a cross-type arrangement of the fixing and securing devices.

According to one variation, the devices for fixing the side flaps are on one only of the two flaps, on the outer surface of the flap towards its free end, making it possible to secure the ends of the flaps by overlapping.

According to another variation, the devices for securing the flaps are provided at each end of the side flaps, on the outer visible side of the flaps, and protected from damage by a moveable arrangement forming a protective pouch which may be overlapping or edge-to-edge.

Protection from damage may be provided by a removable silicone strip, such as is commonly used.

One thus obtains all of the decisive technical advantages described above: a unique sanitary towel with side flaps designed to form a protective wrapper before use and a disposable packet for throwing the towel away after use. Finally, these side flaps also provide an additional means for securing the towel to the wearer's underwear and for ensuring that it is fully protected while the towel is

DESCRIPTION OF DRAWING

The invention's other purposes, properties and advantages will be clear from the explanatory description that follows, with reference to the appended drawings of the different variations of the invention. These drawings are provided as illustrations only, and shall in no way limit the scope of the invention. In the drawings:

FIG. 1 is an underview of a sanitary towel with side flaps;

FIG. 2 is a simple representation of how the sanitary towel is folded inwardly, and of the way in which the side flaps are folded to form a packaging or disposable packet shown in FIG. 3;

FIG. 3 is a diagram of the towel in folded position, ready to be disposed of after use;

FIG. 4 shows a variation of the invention: the towel's side flaps form an integral part of a protective pouch in which the towel is packaged before use;

FIG. 5 shows the sanitary towel after the protective pouch has been opened and the flaps unfolded;

FIG. 6 shows the sanitary towel of FIG. 5 in the position of use, cross section view;

FIG. 7 shows a cross section view in accordance with line VII—VII of FIG. 4;

FIG. 8 shows a similar view to that of FIG. 7, of another variation;

FIG. 9 again shows a cross section view similar to those in FIGS. 7 and 8, of another variation.

DESCRIPTION OF PRESENTLY PREFERRED EMBODIMENTS

With reference to FIG. 1, we have shown a sanitary or similar towel for feminine hygiene featuring side flaps.

This towel is represented by the general reference number 1 and features an absorbent pad, reference 2, to absorb fluids; it is fully contained inside the sheath, 4, the fluid receiving portion of which (i.e., that portion opposite the visible part in FIG. 1) at least is permeable to fluids. In general the part of the sheath opposite the part that receives the fluids, i.e. the part that is fixed to the underwear as is visible in FIG. 1, is made either of a fluid-impermeable material or a fluid-permeable material. In the latter instance, a layer (not shown in the drawing for the sake of simplicity) of fluid-impermeable material is sandwiched between the absorbent pad 2 and the part of the sheath 4 which is in contact with the underwear. The absorbent pad 2 may be preformed, for example to a general biconcave shape, as shown in FIG. 1, and which is commonly seen in sanitary towels. Alternatively, the absorbent pad may be pre-formed to a rectangular shape, narrower at the back, also commonly seen in sanitary towels.

This system also features side flaps 6 and 8, which extend transversally from the central part of the absorbent pad 2 and from its sheath 4. These side flaps 6 and 8 are large enough to be folded around the outside of the wearer's underwear. They may also feature devices for fixing the flaps to the outside of the underwear (references 10 and 12), thus providing full protection for the underwear.

These side flaps 6 and 8 are designed to form, after the sanitary towel (2, 4) has been used, a disposable packet, 20, as shown in FIG. 3, by folding the side flaps 6, 8 over the towel, 2, 4, which have also been folded together.

This is further facilitated by the fact that, in the example shown, the part of the sheath 4 which is in contact with the underwear, which is the side visible in FIG. 1, has at its front end 4a and its back end 4b devices for temporarily securing them to the underwear, for example the adhesive patches 14 and 16. These, with the fixing devices 10 and 12 of flaps 6 and 8, form an arrangement in the form of a cross. This cross-form arrangement is very useful, in that, when the towel is folded, the absorbent pad 2 inside the sheath 4 can be secured in the folded position by means of devices 14 and 16 at the front and back ends, 4a and 4b, respectively. It is then easy to fold flaps 6 and 8 over the folded buffer element, to achieve the configuration of FIG. 3 of a disposable packet.

With this arrangement, there is no need for a separate wrapper in order to be able to dispose of the used towel conveniently.

Devices 10 and 12 may be placed, as shown in FIGS. 1 and 2, on the same side as patches 14 and 16, so that the flaps can be stuck directly to the underwear after they are folded. However, they may be placed in other ways as well. For example, one of the two devices may be placed on the side opposite 12. Securing is then obtained when the flaps overlap each other. It is possible to have only one device, 10 or 12.

With reference to FIG. 4, we have shown a variation of the towel with its wrapper incorporated, meeting the specifications of the invention for which we have used the same reference number as in FIG. 1 with 100 added for the elements fulfilling the same function. According to the invention, side flaps 106 and 108 are an integral part of protective pouch 100, in which the unused towel, 102, is packaged.

The protective pouch 100 features the pre-stamped devices 122, 124 and 126, e.g. the pre-stamped lines that enable one to release side flaps 106 and 108 when the protective pouch 100 is opened. As can be clearly seen, this gives one an open, unfolded sanitary towel, as shown in FIG. 5. Temporary securing devices 110 and 112 of flaps 106 and 108 are arranged as in FIG. 1, as are devices 114 and 116 of front end and back end of sheath 104 containing absorbent buffer element 102. Securing devices 110, 112, 114 and 116 are thus arranged in a cross pattern.

The central part 128 of device 101 forming the sanitary towel features contains no securing devices (e.g. adhesive strips), which makes this central part very flexible.

Moreover, it can be seen that in this variation, the moveable securing devices 110 and 112 are temporarily protected from damage by protective devices 130 and 132, which consist, for example, of silicone strips.

Once the protective pouch 100 is opened by means of pre-stamped lines 122, 124 and 126, and unfolded as shown in FIG. 5, all one has to do is remove protective devices 130 and 132 in order to be able to secure flaps 106 and 108 to the outside of the underwear 140, possibly overlapping flaps 106 and 108, as is clearly shown in FIG. 6. Moveable securing devices 112 of flap 108, for example, placed on the inside, will be applied against the underwear 140, while securing devices 110 of flap 106, for example placed on the outside,overlapping, on flap 108, are secured to flap 108 itself. In another variation, the devices 112 could be eliminated.

As shown in FIGS. 4 to 6, flaps 106 and 108 are preferably formed by a single strip 142, which can be clearly seen in FIGS. 5 and 6, and which is made of a fluid-resistant material like polythene film. Obviously, any other type of suitable material could also be used. This strip 142 is securely fixed to sheath 104 containing absorbent element 102. This can be easily done by gluing, for example by depositing one or more lines of glue 144, clearly visible in FIG. 7.

The protective pouch 100, with strip 142, is manufactured according to a process derived from a conventional method for manufacturing individual packagings for folded towels.

This process consists of wrapping the manufactured towels, which have first been folded in two or three, in a sheet of polythene or other material.

The towel is placed in the center of the sheet. Then, the edges of the sheet are folded over the towel, one over the other. The folded edges are sealed at the central part of the sheet, along the edges perpendicular to the axis of the folds. Finally, the folded ends are sealed together parallel to this axis.

The same procedure is followed if one or more lines of glue 144 are to be deposited on the sheet 142 designed to form the protective pouch 100, or on the sheath 104 containing the buffer element 102, forming the sanitary towel, so as to fix these two pieces together.

In addition, pre-cut lines 122, 124 and 126 along the sealed edges of protective pouch 100 ensure that it is correctly torn to form side flaps 106 and 108. Instead of pre-cut lines, one could also have a temporary seal along lines 124 and 126. Obviously, this procedure is modified for achieving the moveable securing devices 110 and 112 of flaps 106 and 108, for example by applying adhesive patches which are protected from damage by the appropriate protective devices 130 and 132, such as silicone strips on at least one side.

Different variations of this protective pouch are possible, and are shown in cross section in FIGS. 7 to 9, along the same line VII—VII of FIG. 4. In the variations shown in FIGS. 4, 5 and 7, the protective pouch 100 is made with the seal, between securing devices 110 and 112.

In the variation shown in FIG. 8, the side flaps 106 and 108 are fixed in an overlapping position, for example by heat sealing in the case where flaps 106 and 108 are made of a sheet of polythene, which is heat sealable, with this seal line bearing the reference 152.

A simplified variation is also possible, as shown in FIG. 9, according to which only one of the side flaps 106 and 108, for example 106, has a securing device 110 which is not protected and which is used to close the protective pouch 100 by the overlapping of flap 108 over the outer side of flap 106. Protective pouch 100 is then opened simply by separating flap 108 from flap 106. The inner side of flap 108, which faces device 110, may be treated with a suitable substance such as a lacquer so that it could be detached without tearing off device 110 of flap 106. Flaps 106 and 108 can then be fixed to each other outside of the underwear 140 by another overlapping of flaps 106 108 in the same way.

Of course, the invention includes all of the devices which are technical equivalents of the devices described, as well as their various combinations. For example, instead of using adhesive patches for securing devices 110 and 112, 114 and 116, Velcro type fastenings may be used.

Moreover, the side flaps may be made of any material. Nevertheless, it is preferable that side flaps 106 and 108 be part of the sheath 104-buffer element 102 assembly. These side flaps 106 and 108 may be made of a single strip 142 of impermeable material, to provide the underwear with complete protection against stains.

The impermeable material used to make the side flaps may be covered with an absorbent material so that drops of liquid deposited on the flaps do not stain the underwear. A good solution would be to use a complete formed of a polythene or other plastic film and a sheet of non-woven material.

The non-woven material should preferably be made from heat sealable, hemophilically treated fibers and should be soft to the touch.

The non-woven material may be joined to the film by hot melt sticking, extrusion of a polythene film on the non-woven material or by hot-pressing.

It is claimed:

1. A sanitary article for feminine hygiene comprising an absorbent member enveloped within a sheath having first and second longitudinally extending edges, first and second transverse ends, a body contacting side and a garment contacting side with said sheath being at least fluid permeable on said body contacting side; a single piece of flexible fluid-impermeable material having at least a first end and a second end, with the fluid-impermeable material being connected to said sheath-enveloped absorbent member in such a manner that said first end and said second end of said flexible fluid-impermeable material extends beyond respectively said first and said second longitudinally extending edges of said absorbent member enveloped in said sheath so as to form a first side flap and a second side flap with each of said side flaps having one longitudinally extending free edge, one longitudinally extending edge adjacent one of said first or said second longitudinally extending edges of said sheath which envelops said absorbent member to form a fold axis for the side flaps with said absorbent member, and transverse ends; and at least one fastening means attached to at least one of said side flaps; wherein said side flaps are each of a sufficient size so that said side flaps initially are an integral part of a protective pouch for said sanitary article, said side flaps forming the pouch by the presence of a seal joining together said longitudinally extending free edges of said first and said second side flaps and a seal joining together said transverse ends of said first and said second side flaps, with each of said seals being releasable upon the application of a predetermined force thereto; and said side flaps being of a sufficient size so that when said longitudinally extending free edges of said side flaps are no longer releasably sealed, said side flaps selectively (1) extend externally around a crotch portion of an undergarment and (2) fold in overlapping relationship over said absorbent member when said absorbent member is folded over onto itself such that said at least one fastening means serves to secure said side flaps in place in relation to each other and said absorbent member so as to form a disposable packet containing said absorbent member.

2. A sanitary article according to claim 1 wherein said seal joining said longitudinally free edges of said side flaps is formed along pre-stamped lines so as to provide a releasable seal.

3. A sanitary article according to claim 1 wherein said transverse ends of said side flaps are releasably joined between said fold axis for said side flaps and said longitudinally extending free edges of said side flaps.

4. A sanitary article according to claim 1 wherein said sheath contains at least one fastening means on each area of said sheath which overlies each of said first and said second transverse ends of said garment contacting side of said absorbent member and said at least one fastening means on said at least one side flap is positioned in the proximity of said free longitudinally extending edge of said at least one side flap.

5. A sanitary article according to claim 1 wherein said at least one fastening means is present on only one of said side flaps.

6. A sanitary article according to claim 1 wherein said at least one fastening means has a removable protective strip of material overlying said fastening means.

7. A sanitary article according to claim 6 wherein said removable protective strip of material is a silicone strip.

8. A sanitary article according to claim 1 wherein said single piece of fluid impermeable material from which said side flaps are formed is overlaid with an absorbent material on one side thereof.

* * * * *